United States Patent
Adams (10) Patent No.: US 9,730,715 B2
(45) Date of Patent: Aug. 15, 2017

(54) SHOCK WAVE GUIDE WIRE (71) Applicant: SHOCKWAVE MEDICAL, INC., Fremont, CA (US)

(72) Inventor: John M. Adams, Snohomish, WA (US)

(73) Assignee: SHOCKWAVE MEDICAL, INC., Fremont, CA (US)

(*) Notice: Subject to any disclaimer, the term of this patent is extended or adjusted under 35 U.S.C. 154(b) by 72 days.

(21) Appl. No.: 14/273,063

(22) Filed: May 8, 2014

(65) Prior Publication Data
US 2015/0320432 A1 Nov. 12, 2015

(51) Int. Cl.
A61B 17/22 (2006.01)
A61M 25/10 (2013.01)
A61M 25/09 (2006.01)

(52) U.S. Cl.
CPC .. *A61B 17/22004* (2013.01); *A61B 17/22012* (2013.01); *A61B 17/22022* (2013.01); *A61M 25/09* (2013.01); *A61M 25/104* (2013.01); *A61B 2017/22001* (2013.01); *A61B 2017/22042* (2013.01); *A61B 2017/22094* (2013.01);
(Continued)

(58) Field of Classification Search
CPC ........ A61B 17/22004; A61B 17/22012; A61B 17/22022; A61B 17/225; A61B 2017/22001; A61B 2017/22094; A61B 2017/22042; A61M 25/104; A61M 25/09; A61M 2025/09175
See application file for complete search history.

(56) References Cited

U.S. PATENT DOCUMENTS 3,413,976 A 12/1968 Roze
3,785,382 A 1/1974 Schmidt-Kloiber et al.
3,902,499 A 9/1975 Shene
(Continued)

FOREIGN PATENT DOCUMENTS

DE 3038445 A1 5/1982
EP 0442199 A2 8/1991
(Continued)

OTHER PUBLICATIONS

International Search Report and Written Opinion received for PCT Patent Application No. PCT/US2015/029088, mailed on Jul. 16, 2015, 13 pages.
(Continued)

Primary Examiner — Katherine Rodjom
(74) Attorney, Agent, or Firm — Morrison & Foerster LLP (57) ABSTRACT A guide wire, for use, for example, in guiding an elongated catheter through an artery or vein of a mammalian body having a stenosis and/or an occlusion therein, includes an elongated conductor having a longitudinal dimension, a proximal end and a distal end. The guide wire further includes an insulator overlying the elongated conductor. The insulator exposes a portion of the longitudinal dimension of the elongated conductor to form an electrode. The elongated conductor is arranged to be connected to a source of high voltage pulses to cause electrical arcs at the electrode that in turn form steam bubbles and shock waves to break the stenosis and/or open the occlusion and permit the guide wire to pass there through. Other embodiments are directed to a system including the guide wire and a method of using the guide wire.

17 Claims, 7 Drawing Sheets (52) U.S. Cl.
CPC ............ *A61M 2025/09175* (2013.01); *A61M 2210/12* (2013.01)

(56) References Cited

U.S. PATENT DOCUMENTS

| | | |
|---|---|---|
| 4,027,674 A | 6/1977 | Tessler et al. |
| 4,662,126 A | 5/1987 | Malcolm |
| 4,671,254 A | 6/1987 | Fair |
| 4,685,458 A | 8/1987 | Leckrone |
| 4,809,682 A | 3/1989 | Forssmann et al. |
| 5,009,232 A | 4/1991 | Hassler et al. |
| 5,078,717 A | 1/1992 | Parins et al. |
| 5,103,804 A | 4/1992 | Abele et al. |
| 5,125,928 A * | 6/1992 | Parins ................ A61B 18/1492 606/48 |
| 5,152,767 A | 10/1992 | Sypal et al. |
| 5,152,768 A | 10/1992 | Bhatta |
| 5,176,675 A | 1/1993 | Watson et al. |
| 5,246,447 A | 9/1993 | Rosen et al. |
| 5,281,231 A | 1/1994 | Rosen et al. |
| 5,324,255 A | 6/1994 | Passafaro et al. |
| 5,336,234 A | 8/1994 | Vigil et al. |
| 5,364,393 A | 11/1994 | Auth et al. |
| 5,368,591 A | 11/1994 | Lennox et al. |
| 5,395,335 A | 3/1995 | Jang |
| 5,417,208 A | 5/1995 | Winkler |
| 5,425,735 A | 6/1995 | Rosen et al. |
| 5,472,406 A | 12/1995 | de la Torre et al. |
| 5,582,578 A | 12/1996 | Zhong et al. |
| 5,603,731 A | 2/1997 | Whitney |
| 5,609,606 A | 3/1997 | O'Boyle |
| 5,662,590 A | 9/1997 | De et al. |
| 5,697,281 A | 12/1997 | Eggers et al. |
| 5,735,811 A | 4/1998 | Brisken |
| 6,007,530 A | 12/1999 | Doernhoefer et al. |
| 6,033,371 A | 3/2000 | Torre et al. |
| 6,083,232 A | 7/2000 | Cox |
| 6,186,963 B1 | 2/2001 | Schwarze et al. |
| 6,210,404 B1 | 4/2001 | Shadduck |
| 6,210,408 B1 * | 4/2001 | Chandrasekaran A61B 18/1492 606/41 |
| 6,217,531 B1 | 4/2001 | Reitmajer |
| 6,277,138 B1 | 8/2001 | Levinson et al. |
| 6,287,272 B1 | 9/2001 | Brisken et al. |
| 6,352,535 B1 | 3/2002 | Lewis et al. |
| 6,367,203 B1 | 4/2002 | Graham et al. |
| 6,371,971 B1 | 4/2002 | Tsugita et al. |
| 6,398,792 B1 | 6/2002 | O'Connor |
| 6,406,486 B1 | 6/2002 | De La Torre et al. |
| 6,514,203 B2 | 2/2003 | Bukshpan |
| 6,524,251 B2 | 2/2003 | Rabiner et al. |
| 6,589,253 B1 | 7/2003 | Cornish et al. |
| 6,607,003 B1 | 8/2003 | Wilson |
| 6,638,246 B1 | 10/2003 | Naimark et al. |
| 6,652,547 B2 | 11/2003 | Rabiner et al. |
| 6,736,784 B1 | 5/2004 | Menne et al. |
| 6,740,081 B2 | 5/2004 | Hilal |
| 6,755,821 B1 | 6/2004 | Fry |
| 6,989,009 B2 | 1/2006 | Lafontaine |
| 7,241,295 B2 | 7/2007 | Maguire |
| 7,505,812 B1 | 3/2009 | Eggers et al. |
| 7,569,032 B2 | 8/2009 | Naimark et al. |
| 7,873,404 B1 * | 1/2011 | Patton .................... A61B 6/504 600/433 |
| 8,556,813 B2 | 10/2013 | Cioanta et al. |
| 8,728,091 B2 | 5/2014 | Hakala et al. |
| 8,747,416 B2 | 6/2014 | Hakala et al. |
| 8,888,788 B2 | 11/2014 | Hakala et al. |
| 2001/0044596 A1 | 11/2001 | Jaafar |
| 2002/0177889 A1 | 11/2002 | Brisken et al. |
| 2003/0229370 A1 | 12/2003 | Miller |
| 2004/0044308 A1 | 3/2004 | Naimark et al. |
| 2004/0097996 A1 | 5/2004 | Rabiner et al. |
| 2004/0254570 A1 | 12/2004 | Hadjicostis et al. |
| 2005/0015953 A1 | 1/2005 | Keidar |
| 2005/0021013 A1 | 1/2005 | Visuri et al. |
| 2005/0228372 A1 | 10/2005 | Truckai et al. |
| 2005/0251131 A1 | 11/2005 | Lesh |
| 2006/0004286 A1 | 1/2006 | Chang et al. |
| 2006/0184076 A1 | 8/2006 | Gill et al. |
| 2006/0190022 A1 | 8/2006 | Beyar et al. |
| 2007/0088380 A1 | 4/2007 | Hirszowicz et al. |
| 2007/0239082 A1 | 10/2007 | Schultheiss et al. |
| 2007/0244423 A1 | 10/2007 | Zumeris et al. |
| 2007/0255270 A1 | 11/2007 | Carney |
| 2008/0097251 A1 | 4/2008 | Babaev |
| 2009/0247945 A1 | 10/2009 | Levit et al. |
| 2009/0254114 A1 | 10/2009 | Hirszowicz et al. |
| 2009/0312768 A1 | 12/2009 | Hawkins et al. |
| 2010/0036294 A1 | 2/2010 | Mantell et al. |
| 2010/0121322 A1 | 5/2010 | Swanson |
| 2010/0305565 A1 | 12/2010 | Truckai et al. |
| 2011/0034832 A1 | 2/2011 | Cioanta et al. |
| 2011/0118634 A1 | 5/2011 | Golan |
| 2011/0166570 A1 | 7/2011 | Hawkins et al. |
| 2011/0208185 A1 | 8/2011 | Diamant et al. |
| 2011/0295227 A1 | 12/2011 | Hawkins et al. |
| 2012/0221013 A1 | 8/2012 | Hawkins et al. |
| 2013/0030431 A1* | 1/2013 | Adams ............. A61B 17/22022 606/41 |
| 2013/0030447 A1 | 1/2013 | Adams |
| 2014/0005576 A1 | 1/2014 | Adams et al. |
| 2014/0039513 A1 | 2/2014 | Hakala et al. |
| 2014/0052145 A1 | 2/2014 | Adams et al. |
| 2014/0052147 A1 | 2/2014 | Hakala et al. |
| 2014/0074111 A1* | 3/2014 | Hakala ............. A61B 17/22022 606/127 |
| 2014/0074113 A1 | 3/2014 | Hakala et al. |
| 2014/0243820 A1 | 8/2014 | Adams et al. |
| 2015/0073430 A1 | 3/2015 | Hakala et al. |
| 2015/0238208 A1 | 8/2015 | Adams et al. |
| 2016/0184570 A1 | 6/2016 | Grace et al. |

FOREIGN PATENT DOCUMENTS

| | | |
|---|---|---|
| EP | 0571306 A1 | 11/1993 |
| JP | 62-275446 A | 11/1987 |
| JP | 6-125915 A | 5/1994 |
| JP | 7-47135 A | 2/1995 |
| JP | 10-99444 A | 4/1998 |
| JP | 10-513379 A | 12/1998 |
| JP | 2002-538932 A | 11/2002 |
| JP | 2004-81374 A | 3/2004 |
| JP | 2005-95410 A | 4/2005 |
| JP | 2005-515825 A | 6/2005 |
| JP | 2006-516465 A | 7/2006 |
| JP | 2007-532182 A | 11/2007 |
| WO | 96/24297 A1 | 8/1996 |
| WO | 2004/069072 A2 | 8/2004 |
| WO | 2005/099594 A1 | 10/2005 |
| WO | 2006/127158 A2 | 11/2006 |
| WO | 2007/149905 A2 | 12/2007 |
| WO | 2009/121017 A1 | 10/2009 |
| WO | 2009/152352 A2 | 12/2009 |
| WO | 2010/014515 A2 | 2/2010 |
| WO | 2011/143468 A2 | 11/2011 |
| WO | 2012/025833 A2 | 3/2012 |
| WO | 2016/109739 A1 | 7/2016 |

OTHER PUBLICATIONS

Notice of Allowance received for U.S. Appl. No. 13/049,199, mailed on Jan. 13, 2015, 4 pages.
Non Final Office Action received for U.S. Appl. No. 14/515,130, mailed on Jan. 14, 2016, 16 pages.
Notice of Allowance received for U.S. Appl. No. 14/515,130, mailed on May 2, 2016, 8 pages.
Non Final Office Action received for U.S. Appl. No. 13/534,658, mailed on Mar. 11, 2016, 12 pages.
Extended European Search Report received for European Patent Application No. 13827971.6, mailed on Apr. 12, 2016, 8 pages.
Non Final Office Action received for U.S. Appl. No. 12/482,995, mailed on Aug. 13, 2014, 10 pages.

(56) References Cited

OTHER PUBLICATIONS

Final Office Action received for U.S. Appl. No. 13/049,199 mailed on Aug. 11, 2014, 8 pages.
Non Final Office Action received for U.S. Appl. No. 13/465,264, mailed on Oct. 29, 2014, 13 pages.
Non Final Office Action received for U.S. Appl. No. 13/646,570, mailed on Oct. 29, 2014, 10 pages.
Non-Final Office Action received for U.S. Appl. No. 13/646,583, mailed on Oct. 31, 2014, 8 pages.
Notice of Allowance received for U.S. Appl. No. 13/831,543, mailed on Oct. 8, 2014, 14 pages.
Non-Final Office Action received for U.S. Appl. No. 14/271,342, mailed on Sep. 2, 2014, 6 pages.
Doug Hakala, "Unpublished U.S. Appl. No. 14/515,130, filed Oct. 15, 2014, titled "Low Profile Electrodes for an Angioplasty Shock Wave Catheter"".
Office Action Received for Japanese Patent Application No. 2011-513694, mailed on Jun. 10, 2014, 2 pages of Official Copy only (See Communication under 37 CFR § 1.98(a) (3)).
Written Opinon received for PCT Patent Application No. PCT/US2009/047070, mailed on Jan. 19, 2010, 5 pages.
International Preliminary Report on Patentability received for PCT Patent Application No. PCT/US2009/047070, mailed on Dec. 23, 2010, 7 pages.
Notice of Acceptance Received for Australian Patent Application No. 2009257368, mailed on Aug. 28, 2014, 2 pages.
Office Action received for Australian Patent Application No. 2009257368, issued on Apr. 28, 2014, 4 pages.
Office Action received for Australian Patent Application No. 2009257368, issued on Jul. 31, 2013, 4 pages.
Extended European Search Report (includes Supplementary European Search Report and Search Opinion) received for European Patent Application No. 09763640.1, mailed on Oct. 10, 2013, 5 pages.
Office Action received for Japanese Patent Application No. 2011-513694, mailed on Aug. 27, 2013, 6 pages (3 pages of English Translation and 3 pages of Official copy).
International Search Report received for PCT Patent Application No. PCT/US2009/047070, mailed on Jan. 19, 2010, 4 pages.
International Preliminary Report on Patentability received for PCT Patent Application No. PCT/US2011/047070, mailed on Feb. 21, 2013, 7 pages.
International Written Opinion received for PCT Patent Application No. PCT/US2011/047070, mailed on May 1, 2012, 5 pages.
International Search Report and Written Opinion received for PCT Patent Application No. PCT/US2013/031805 mailed on May 20, 2013, 13 pages.
International Search Report and Written Opinion received for PCT Patent Application No. PCT/US2013/039987, mailed on Sep. 23, 2013, 15 pages.
International Search Report and Written Opinion received for PCT Patent Application No. PCT/US2013/048277, mailed on Oct. 2, 2013, 14 pages.
Final Office Action received for U.S. Appl. No. 13/049,199, mailed on Apr. 4, 2012, 10 pages.
Non Final Office Action received for U.S. Appl. No. 13/049,199, mailed on Dec. 12, 2011, 10 pages.
Non-Final Office Action received for U.S. Appl. No. 13/049,199, mailed on Feb. 4, 2014, 8 pages.
Non-Final Office Action received for U.S. Appl. No. 14/061,554, mailed on Mar. 12, 2014, 14 pages.
Notice of Allowance received for U.S. Appl. No. 14/061,554, mailed on Apr. 25, 2014, 8 pages.
Final Office Action received for U.S. Appl. No. 12/482,995, mailed on Feb. 20, 2014, 11 pages.
Final Office Action received for U.S. Appl. No. 12/482,995, mailed on Jul. 22, 2011, 14 pages.
Non Final Office Action received for U.S. Appl. No. 12/482,995, mailed on Jul. 12, 2013, 11 pages.
Non Final Office Action received for U.S. Appl. No. 12/482,995, mailed on Feb. 11, 2011, 27 pages.
Final Office Action received for U.S. Appl. No. 12/501,619, mailed on Feb. 21, 2012, 12 pages.
Non Final Office Action received for U.S. Appl. No. 12/501,619, mailed on Nov. 3, 2011, 10 pages.
Non-Final Office Action received for U.S. Appl. No. 12/501,619, mailed on Jan. 28, 2014, 10 pages.
Adams et al., U.S. Appl. No. 13/534,658, filed Jun. 27, 2012, titled "Shock Wave Balloon Catheter with Multiple Shock Wave Sources".
Adams et al., Unpublished U.S. Appl. No. 14/271,342, filed May 6, 2014, titled "Shock Wave Balloon Catheter with Multiple Shock Wave Sources", 21 pages.
Hakala et al., U.S. Appl. No. 13/831,543, filed Mar. 14, 2013, titled "Low Profile Electrodes for an Angioplasty Shock Wave Catheter", 52 pages.
Hakala et al., U.S. Appl. No. 14/061,554, filed Oct. 23, 2013, titled "Low Profile Electrodes for an Angioplasty Shock Wave Catheter".
Rosenschein et al., "Shock-Wave Thrombus Ablation, a New Method for Noninvasive Mechanical Thrombolysis", The American Journal of Cardiology, vol. 70, Nov. 15, 1992, pp. 1358-1361.
Zhong et al., "Transient Oscillation of Cavitation Bubbles Near Stone Surface During Electohydraulic Lithotripsy", Journal of Endourology, vol. 11, No. 1, Feb. 1997, pp. 55-61.
Hakala, Doug, U.S. Appl. No. 15/220,999, filed Jul. 27, 2016, titled "Low Profile Electrode for an Angioplasty Shock Wave Catheter".
Final Office Action received for U.S. Appl. No. 13/534,658, mailed on Aug. 23, 2016, 11 pages.

\* cited by examiner

SHOCK WAVE GUIDE WIRE

BACKGROUND

The present invention relates to a treatment and system for crossing an arterial lesion in order to dilate the lesion and restore normal blood flow in the artery. Such devices and methods may be used as part of a balloon angioplasty procedure. Calcified lesions require high pressures (sometimes as high as 10-15 or even 30 atmospheres) to break the calcified plaque and push it back into the vessel wall. With such pressures comes trauma to the vessel wall which can contribute to vessel rebound, dissection, thrombus formation, and a high level of restenosis. Non-concentric calcified lesions can result in undue stress to the free wall of the vessel when exposed to high pressures.

Angioplasty balloons have been employed to treat such lesions. When inflated to high pressures, angioplasty balloons can have a specific maximum diameter to which they will expand. Generally, the opening in the vessel under a concentric lesion will typically be much smaller. As the pressure is increased to open the passage way for blood flow, the balloon will be confined to the size of the opening in the calcified lesion (before it is broken open). As the pressure builds, a tremendous amount of energy is stored in the balloon until the calcified lesion breaks or cracks. That energy is then released and results in the rapid expansion of the balloon to its maximum dimension and may stress and injure the vessel walls.

Recently, a new system and method has been contemplated for breaking up calcium deposits in, for example, arteries and veins. Such a system is described, for example in U.S. Patent Publication No. 2009/0312768, Published Dec. 17, 2009. Embodiments described therein include a catheter having balloon, such as an angioplasty balloon, at the distal end thereof arranged to be inflated with a fluid. Disposed within the balloon is a shock wave generator that may take the form of, for example, a pair of electrodes, which are coupled to a high voltage source at the proximal end of the catheter through a connector. When the balloon is placed adjacent a calcified region of a vein or artery and a high voltage pulse is applied across the electrodes, a shock wave is formed that propagates through the fluid and impinges upon the wall of the balloon and the calcified region. Repeated pulses break up the calcium without damaging surrounding soft tissue.

Arteries are sometimes totally occluded with a thrombus, plaque, fibrous plaque, and/or calcium deposits. When this condition is present, the physician must first pass a soft narrow guide wire down the artery and through the occluded area. The guide wire may be as small as 0.014 inches in diameter and usually has a soft flexible tip to help avoid penetrating the artery wall in artery corners. The angioplasty balloon is then fed down the artery on the guide wire to the desired location of the blockage. Unfortunately, many times the physician is faced with a chronic occlusion which is not passable with a guide wire. This occurs when the occlusion is so tight and solid that the soft guide wire cannot penetrate through it. Stiffer guide wires may be used in these cases, but they must be used very carefully because they can easily penetrate the artery wall when forced against the chronic total occlusion.

Guide wires have been proposed that utilize radio frequency energy to open the occlusion. Unfortunately, the heat generated by the radio frequency energy to open the occlusion is intense and can damage the walls of the artery or vessel. The radio frequency energy produces a plasma which burns anything in its path. Hence, such systems must be used carefully and must be continuously moved without pause to avoid artery or vessel damage. Moreover, such an approach requires a centering mechanism that keeps the plasma centered in the artery or vessel. Such centering is difficult to achieve, especially in the corners and bends of the arteries or veins.

Hence, there is a need for an apparatus and procedure for opening a total occlusion enough to permit a guide wire and angioplasty balloon to be fed there through. Most desirably, such an apparatus and procedure would avoid damage the artery or vessel and further be compatible with the use of the aforementioned shock wave catheter systems described above. The present invention addressed these and other issues.

SUMMARY

In one embodiment, a guide wire for use in, for example, guiding an elongated catheter through an artery or vein of a mammalian body having a stenosis and/or an occlusion therein, includes an elongated conductor having a longitudinal dimension, a proximal end and a distal end. The guide wire further includes an insulator overlying the elongated conductor. The insulator exposes a portion of the longitudinal dimension of the elongated conductor to form an electrode. The elongated conductor is arranged to be connected to a source of high voltage pulses to cause electrical arcs at the electrode that in turn form steam bubbles and shock waves to break the stenosis and/or open the occlusion and permit the guide wire to pass there through.

The elongated conductor may have a distal tip end at the distal end of the elongated conductor and the electrode may be at the distal tip end of the elongated conductor. The distal tip end of the elongated conductor may be generally spherical in configuration. The distal tip end may be formed of stainless steel.

The insulator may be formed of Teflon. The elongated conductor and insulator may form a flexible coiled structure at the distal end of the elongated conductor. The distal tip end of the elongated conductor may be generally spherical in configuration.

The guide wire may further include an anchor. The anchor may be releasable to permit the elongated conductor and insulator to be moved longitudinally and rotated.

In another embodiment, a guide wire system, for use, for example, in guiding an elongated catheter through an artery or vein of a mammalian body having a stenosis and/or an occlusion therein includes a guide wire including an elongated conductor having a longitudinal dimension, a proximal end and a distal end and an insulator overlying the elongated conductor. The insulator exposes a portion of the longitudinal dimension of the elongated conductor to form an electrode. The system further includes a source of high voltage pulses to cause electrical arcs at the electrode that in turn form steam bubbles and shock waves to break the stenosis and/or open the occlusion.

The source of high voltage may be arranged to provide the elongated conductor with a high electrical voltage at a comparatively low initial current through the elongated conductor and terminate the high electrical voltage in response to a comparatively high current through the elongated conductor.

The source of high voltage may be arranged to deliver a first electrical voltage to the electrode that grows a bubble at the electrode and then thereafter to deliver a second electrical voltage to the electrode to create an arc at the electrode and to rapidly expand the bubble to form a shock wave.

The elongated conductor of the guide wire has a distal tip end at the distal end of the elongated conductor and wherein the electrode may be at the distal tip end of the elongated conductor. The distal tip end of the elongated conductor may be generally spherical in configuration. The distal tip end may be formed of stainless steel. The insulator may be formed of Teflon.

The elongated conductor and insulator of the guide wire may be configured to form a flexible coiled structure at the distal end of the elongated conductor. The distal tip end of the elongated conductor may be generally spherical in configuration.

The system may further include an anchor, the anchor being releasable to permit the elongated conductor and insulator to be moved longitudinally and rotated.

In a still further embodiment, a method for use, for example, in guiding an elongated catheter through an artery or vein of a mammalian body having a stenosis and/or an occlusion therein includes the steps of providing an elongated conductor having a longitudinal dimension, a proximal end, a distal end and an insulator overlying the elongated conductor. The insulator exposes a portion of the longitudinal dimension of the elongated conductor to form an electrode. The method further includes the steps of inserting the elongated conductor into an artery or vein until a stenosis and/or an occlusion is reached and applying at least one high voltage pulse to the elongated conductor to cause at least one electrical arc at the electrode that in turn forms at least one steam bubble and shock wave to break the stenosis and/or open the occlusion.

The step of applying the at least one high voltage pulse to the elongated conductor may include providing the elongated conductor with a high electrical voltage at a comparatively low initial current through the elongated conductor and terminating the high electrical voltage in response to a comparatively high current through the elongated conductor.

The step of applying the at least one high voltage pulse to the elongated conductor may include delivering a first electrical voltage to the electrode that grows a bubble at the electrode and then thereafter delivering a second electrical voltage to the electrode to create an arc at the electrode and to rapidly expand the bubble to form a shock wave.

One variation of a method for opening a vascular occlusion described herein may comprise advancing a shock wave guide wire within the vasculature to contact the vascular occlusion, where the shock wave guide wire comprises an elongated conductor with a conductive distal tip and an insulator overlying the elongate conductor without covering the conductive distal tip, advancing an angioplasty balloon catheter over the shock wave guide wire to the vascular occlusion, generating one or more shock waves using the guide wire to create one or more openings in the occlusion, and advancing the angioplasty balloon catheter into the one or more openings to perform an angioplasty procedure. In some variations, the method may also include attaching a return electrode or pad to a patient's skin. The method may also comprise visualizing the vascular occlusion, for example, by injecting a dye from the angioplasty balloon catheter, and/or confirming the location of the shock wave guide wire and/or the angioplasty balloon catheter prior to generating one or more shock waves. In some variations, the method may further comprising centering the distal tip of the shock wave guide wire within the vascular lumen prior to generating one or more shock waves, where centering the distal tip of the shock wave guide wire may comprise expanding the angioplasty balloon of the angioplasty balloon catheter. Advancing the angioplasty balloon catheter into the one or more openings to perform an angioplasty procedure may comprise inflating the balloon to further open the occlusion. The angioplasty balloon catheter may comprise one or more shock wave electrodes within the balloon and advancing the angioplasty balloon catheter into the one or more openings to perform an angioplasty procedure may comprise generating one or more shock waves within the angioplasty balloon to further open the occlusion.

Another variation of a method for opening a vascular occlusion may comprise advancing a shock wave guide wire within the vasculature to contact the vascular occlusion, where the shock wave guide wire comprises an elongated conductor with a conductive distal tip and an insulator overlying the elongate conductor without covering the conductive distal tip, and generating one or more shock waves using the guide wire to create one or more openings in the occlusion. In some variations, the method may also include attaching a return electrode or pad to a patient's skin. The method may optionally comprise visualizing the vascular occlusion prior to generating one or more shock waves. In some variations, the method may further comprise advancing an angioplasty balloon catheter over the shock wave guide wire to the one or more openings in the vascular occlusion to perform an angioplasty procedure. The angioplasty balloon catheter may comprise one or more shock wave electrodes within the balloon, and advancing the angioplasty balloon catheter into the one or more openings to perform an angioplasty procedure may comprise generating one or more shock waves within the angioplasty balloon to further open the occlusion. Optionally, the method may further comprise centering the distal tip of the shock wave guide wire within the vascular lumen prior to generating one or more shock waves. Centering the distal tip of the shock wave guide wire may comprise expanding the angioplasty balloon of the angioplasty balloon catheter.

BRIEF DESCRIPTION OF THE DRAWINGS

The features of the present invention which are believed to be novel are set forth with particularity in the appended claims. The various described embodiments of the invention, together with representative features and advantages thereof, may best be understood by making reference to the following description taken in conjunction with the accompanying drawings, in the several figures of which like reference numerals identify identical elements, and wherein:

DETAILED DESCRIPTION

Figure 1:
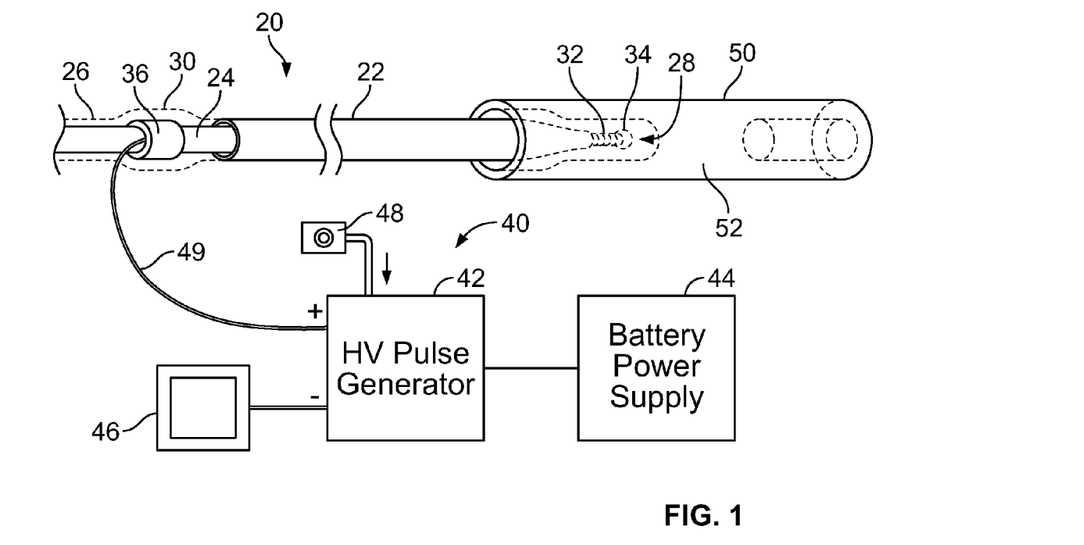
FIG. 1 is a perspective view, with portions cut away, of a shock wave guide wire system embodying aspects of the invention.

FIG. 1 is a partial cut away view of a blood vessel 50 (e.g., an artery or vein) of a heart (or other body part) being treated with a shock wave guide wire system 20 embodying aspects of the invention. The blood vessel has a stenosis or chronic total occlusion 52 being opened by the system 20. The system 20 generally includes a guide wire 22 embodying the invention, and a power source 40.

In this embodiment, the guide wire 22 includes an elongated conductor 24 having a longitudinal dimension with a proximal end 26 and a distal end 28. The guide wire 22 further includes an insulator 30 overlying the elongated conductor. The insulator exposes a portion 32 of the longitudinal dimension of the elongated conductor forming an electrode that terminates with an electrode tip 34 at the distal end 28 of the guide wire 22. The elongated conductor 24 is arranged to be connected to the power source 40 arranged to provide high voltage pulses to cause electrical arcs at the electrode tip 34 that in turn form steam bubbles and shock waves to break the stenosis and/or open the occlusion 52 and permit the guide wire 22 to pass there through.

The power source includes a high voltage pulse generator 42, a battery power supply 44, a return pad or ground patch 46, which may have a larger surface area than the electrode tip of the guide wire, and an on/off control 48. The battery supply 44 lends to the portability and safety of the system 20. The patch 46 is preferably the type that makes broad surface contact with the patient's skin. The power source is connected to the elongated conductor 24 of the guide wire 22 at a metallic ring 36. The ring 36, conductor 24, and power source lead 49 are preferably connected together with solder or a crimp. An additional reusable connector in lead 49 is not shown for simplicity.

The elongated conductor 24 and electrode tip 34 may be formed of stainless steel, for example. The insulator 30 may be formed from Teflon, for example, and arranged to cover the entire elongated conductor 24 except at the distal end 34 to form the exposed electrode portion 32. The electrode tip 34 is preferably generally spherical in shape. The pulse generator 42 is preferably arranged to provide voltage pulses of between about 300 and 3000 volts between the elongated conductor 24 and the patch 46. The duration of the applied pulses is preferably very short, on the order of 0.1 to 2.0 microseconds.

Without wishing to be bound by theory, a monopolar or unipolar electrode arrangement (such as described above) may give rise to a shock wave by generating a plasma arc across an electrolysis bubble. Such arc does not extend to a remote ground patch or return pad (in contrast to a bipolar electrode arrangement, where the arc extends from the electrode to the return electrode). When a voltage is applied to the monopolar electrode, a low level of current may flow between the electrode and return pad, which may cause dissociation of hydrogen and oxygen in the surrounding fluid such that a gas bubble (e.g., an electrolysis bubble) forms at the electrode tip 34. When the applied voltage is increased to a high value (e.g., from about 500 V to about 3000 V), a plasma arc forms at the electrode tip and arcs across the gas bubble to the surrounding fluid. This plasma arc may generate sufficient heat to form a steam bubble in the fluid, the formation of which gives rise to a first shock wave. When the steam bubble collapses, a second shock wave may be formed. In contrast to a bipolar system, the plasma arc does not extend from the electrode tip to the return pad. Since the plasma arc generated by a monopolar system is shorter (e.g., the distance across a gas bubble) than that generated by a bipolar system (e.g., the distance between the first electrode and the return electrode), less heat is generated and therefore, the magnitude of a shock wave generated by a monopolar system may be less than the magnitude of a shock wave generated by a bipolar system. The pulse magnitude, duration, frequency and/or duty cycle of a monopolar system may be adjusted to ensure that a shock wave of sufficient force is generated to soften or crack the occlusion in the blood vessel.

In operation, the guide wire 22 is fed into the blood vessel 50 (e.g., artery or vein) to place the electrode adjacent the occlusion 52. The patch 46 is adhered to the patient's skin to serve as a return path. The on/off switch 48 is then turned on to permit the pulse generator 42 to provide the high voltage pulses to the elongated conductor 24 and hence the electrode portion 32 and electrode tip 34. Each pulse is of sufficient amplitude and duration as mentioned above to cause a gas (steam) bubble to be formed at the electrode tip 34. Each gas bubble in turn causes a shock wave to form with each shock wave causing the opening in the occlusion to become enlarged. With each shock wave, the guide wire 22 may be advanced until the occlusion is crossed. The number of shock waves required will depend upon the size and hardness of the occlusion. Typically, several pulses will be required. Various pulse trains and waveforms may be used to generate one or more shock waves, as may be desired to create an opening in a vascular occlusion. In some variations, the duty cycle of the voltage waveform may be from about 1 Hz to about 2 Hz, or from about 3 to about 5 Hz, e.g., 3 Hz. The pulse widths may be less than or equal to about 3 µs, e.g., from about 0.1 µs to about 2 µs, from about 1 µs to about 2 µs, or less than 2 µs. The magnitude of the voltage pulses may be from about 500 V to about 3000 V. A remote control (not shown) or foot switch or button 48 can be provided for easy turn off by the physician. Both softer thrombus and calcified chronic total occlusions can be opened with the system of FIG. 1.

Figure 11A:
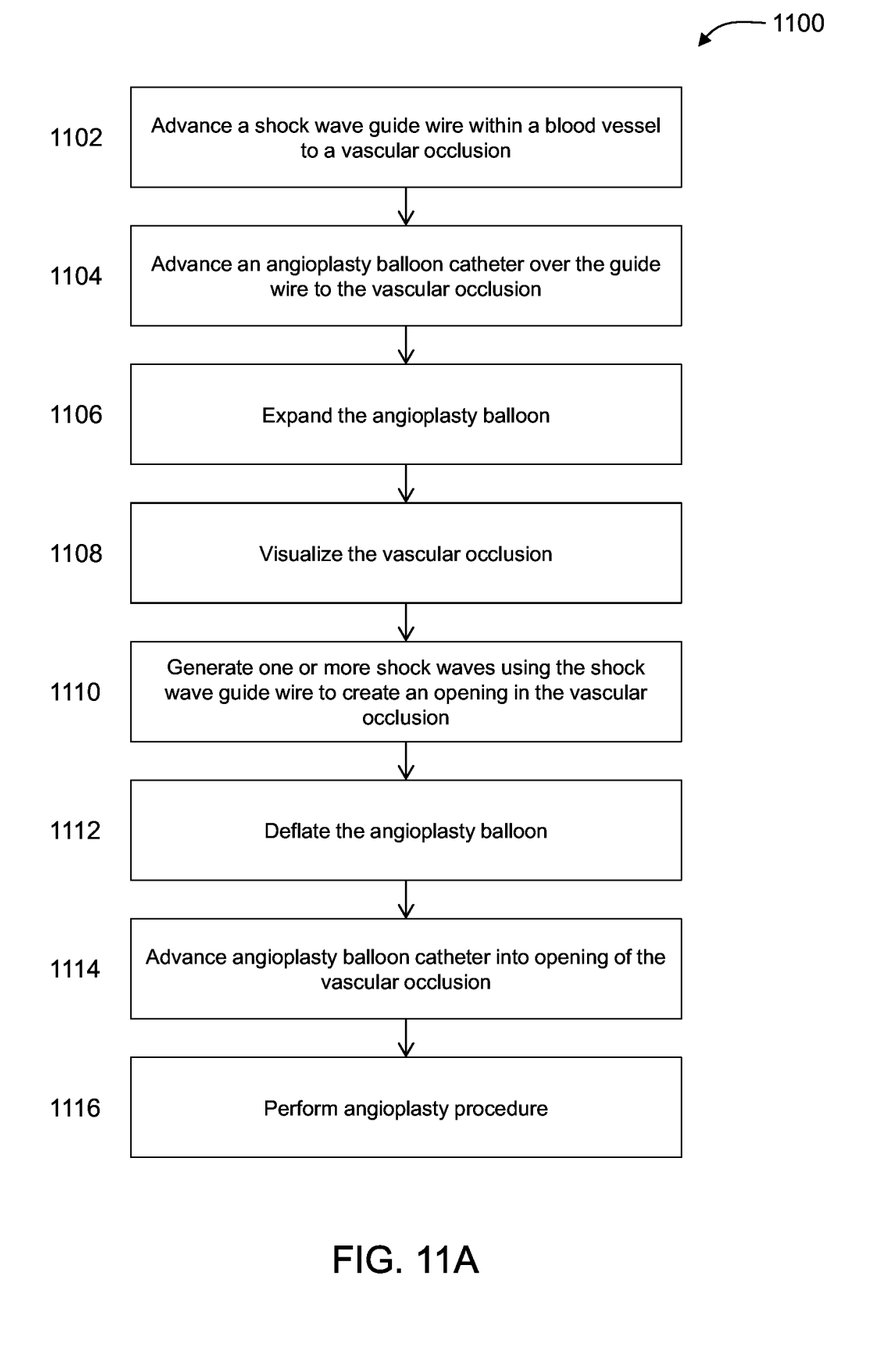
FIG. 11A is a flow diagram that depicts one variation of method that uses a shock wave guide wire system.

One variation of a method of using a shock wave guide wire in a monopolar configuration to create an opening in a vascular occlusion may comprise the steps depicted in the flow diagram of FIG. 11A. Method 1100 may comprise advancing a guide wire 1102 capable of generating one or more shock waves (e.g., any of the guide wires described herein) within a blood vessel to a vascular occlusion (e.g., a chronic total occlusion) and advancing an angioplasty balloon catheter 1104 over the guide wire to the vascular occlusion. Optionally, a sheath or guide catheter may be introduced into the vasculature, and the guide wire and/or angioplasty balloon catheter may be subsequently advanced through the sheath or guide catheter to access the vascular occlusion. The angioplasty balloon catheter may or may not comprise a shock wave generator (e.g., one or more shock wave electrodes) within the angioplasty balloon. The angioplasty balloon may then be expanded 1106 before, after, or simultaneously with visualizing 1108 the vascular occlusion. The vascular occlusion may be visualized, for example, by using a dye that is injected through a guide wire lumen of the angioplasty catheter. Alternatively or additionally, dye may be injected into the vasculature via a sheath or guide catheter through which the guide wire may be advanced. Visualizing the occlusion may help a practitioner to confirm that the shock wave guide wire is in contact with the occlusion. Expanding the angioplasty balloon may help a practitioner center the shock wave guide wire within the vessel lumen. Method 1100 may comprise generating one or more shock waves 1110 using the shock wave guide wire to create an opening in the occlusion (e.g., by activating a pulse generator as described above). Such opening may be confirmed by injecting dye from the angioplasty catheter. Once it has been confirmed that one or more openings has been created within the occlusion, the angioplasty balloon may optionally be deflated 1112 and the angioplasty balloon catheter may be advanced 1114 into the opening of the vascular occlusion. The angioplasty balloon catheter may then be used to perform an angioplasty procedure 1116, with or without the generation of additional shock waves from the guide wire. The angioplasty balloon catheter may soften or crack the calcifications remaining from the occlusion by generating shock waves within the angioplasty balloon (e.g., with shock wave electrodes located within the angioplasty balloon). Alternatively or additionally, the angioplasty balloon catheter may soften or crack calcifications remaining from the occlusion by expanding the angioplasty balloon.

Figure 11B:
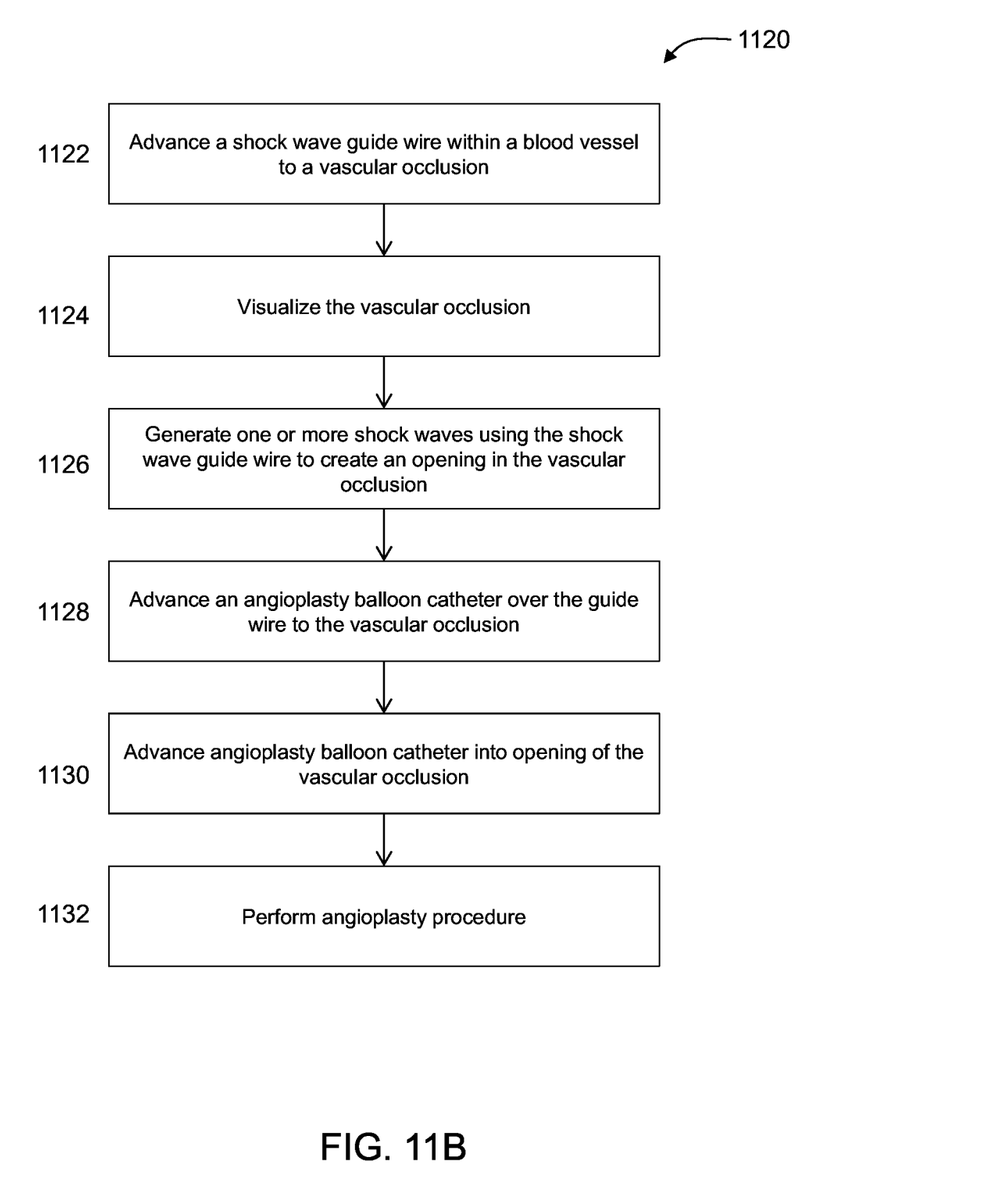
FIG. 11B is a flow diagram that depicts another variation of a method that uses a shock wave guide wire system.

Another variation of a method of using a shock wave guide wire in a monopolar configuration to create an opening in an occlusion may comprise the steps depicted in the flow diagram of FIG. 11B. Method 1120 may comprise advancing a guide wire 1122 capable of generating one or more shock waves (e.g., any of the guide wires described herein) within a blood vessel to a vascular occlusion (e.g., a chronic total occlusion). Optionally, a sheath or guide catheter may be introduced into the vasculature, and the guide wire may be subsequently advanced through the sheath or guide catheter to access the vascular occlusion. The method 1120 may comprise visualizing the occlusion 1124 after the guide wire has been advanced. For example, a dye may be delivered by a catheter (e.g., an angioplasty catheter where the balloon is not inflated) located upstream from the vascular occlusion and/or via a sheath or guide catheter through which the guide wire may be advanced. Visualizing the occlusion may help a practitioner to confirm that the shock wave guide wire is in contact with the occlusion. Method 1120 may comprise generating one or more shock waves 1126 using the shock wave guide wire to create an opening in the occlusion (e.g., by activating a pulse generator as described above). Such opening may be confirmed by using the same or different visualizing techniques of step 1124. Once it has been confirmed that one or more openings has been created within the occlusion, method 1120 may comprise advancing an angioplasty balloon catheter 1128 over the guide wire to the vascular occlusion. The angioplasty balloon catheter may or may not comprise a shock wave generator (e.g., one or more shock wave electrodes) within the angioplasty balloon. The angioplasty balloon catheter may be advanced 1130 into the opening of the vascular occlusion. The angioplasty balloon catheter may then be used to perform an angioplasty procedure 1132, with or without the generation of additional shock waves from the guide wire. The angioplasty balloon catheter may soften or crack the calcifications remaining from the occlusion by generating shock waves within the angioplasty balloon (e.g., with shock wave electrodes located within the angioplasty balloon). Alternatively or additionally, the angioplasty balloon catheter may soften or crack calcifications remaining from the occlusion by expanding the angioplasty balloon.

Figure 2:
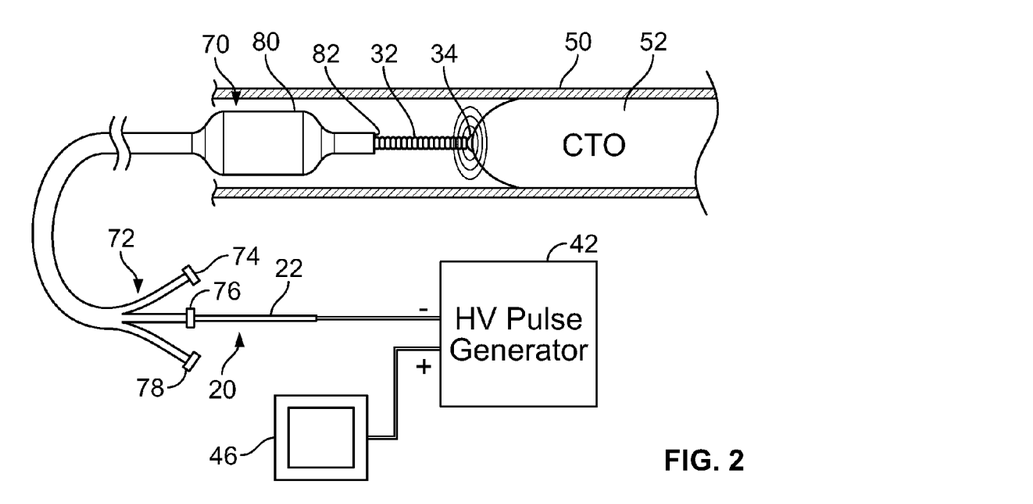
FIG. 2 is a perspective view, with portions cut away, showing further details of the shock wave guide wire system of FIG. 1 in use with an angioplasty catheter.

FIG. 2 is a perspective view, with portions cut away, showing further details of the shock wave guide wire system 20 of FIG. 1 in use with an angioplasty catheter. Here it may be appreciated that the shock wave guide system 20 may be employed to cross the occlusion 52 sufficiently to enable an angioplasty catheter of the type well known in the art to be carried on the guide wire 22 to a position within the occlusion opened by the shock wave guide wire system 20. To that end, the angioplasty balloon catheter includes Luer connectors 74, 76, and 78 at its proximal end 72, an angioplasty balloon 80, and a guide wire lumen 82. The guide wire 22 is introduced onto the catheter 70 through the Luer connector 76 and into the guide wire lumen 82 until it extends through the angioplasty balloon 80 and out the guide wire lumen 82. Once the shock wave guide wire system 20 opens the occlusion sufficiently, the balloon catheter 70 may be advanced down the guide wire to place the balloon 80 within the opening of the occlusion formed by the shock wave guide wire system to further open the occlusion 52 as necessary. FIG. 2 also shows in the alternative negative polarity to the connection 22 and positive to the skin electrode 46.

Figure 3:
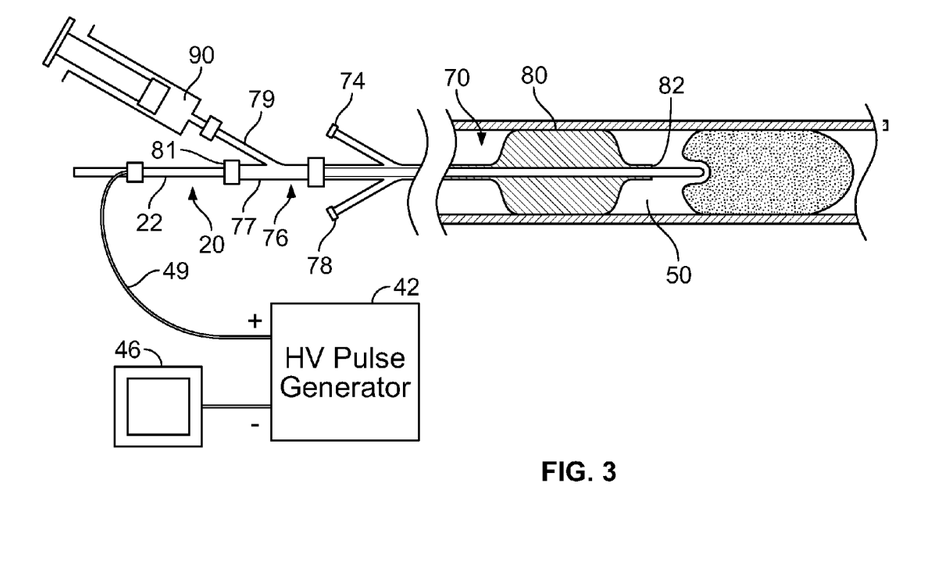
FIG. 3 is a perspective view, with portions cut away, showing still further details of the shock wave guide wire system of FIG. 1 in use with an angioplasty catheter.

FIG. 3 is a perspective view, with portions cut away, showing still further details of the shock wave guide wire system 20 of FIG. 1 in use with the angioplasty catheter 70. Here it may be seen that the Luer connector 76 may include two branches 77 and 79. The branch 77 accepts the guide wire 22. It includes a Tuey-Borst connector 81 that, when turned, clamps down on the guide wire 22. This can be used as an anchor to longitudinally fix the guide wire. However, by loosening the Tuey-Borst connector 81, the insulator 30 and conductor 24 (FIG. 1) of the guide wire 22 may be advanced and even rotated to obtain the most advantageous positioning of the guide wire 22. The other branch 79 of the Luer connector 76 may be attached to a source of saline 90, for example. The saline may be employed to inflate the angioplasty balloon 80 in a manner known in the art to further open the occlusion when it is in its proper position.

Figure 4:
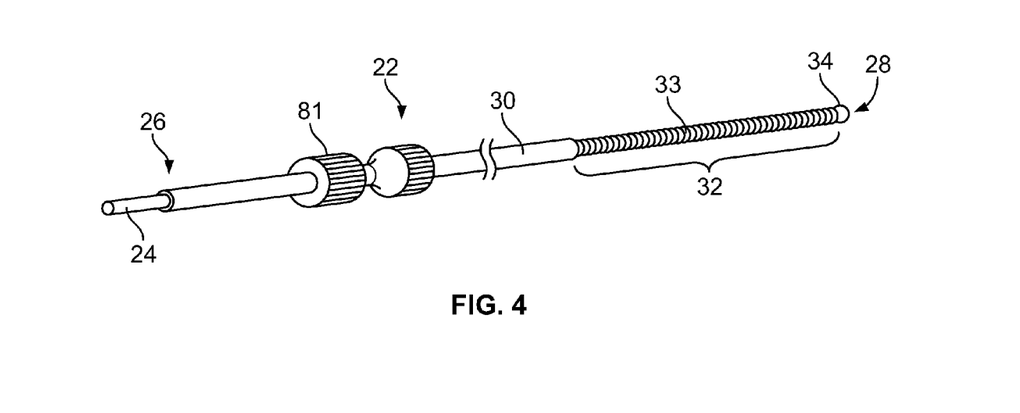
FIG. 4 is a perspective view of the guide wire of the shock wave guide wire system of FIG. 1 illustrating further aspects of the invention.
Figure 5:
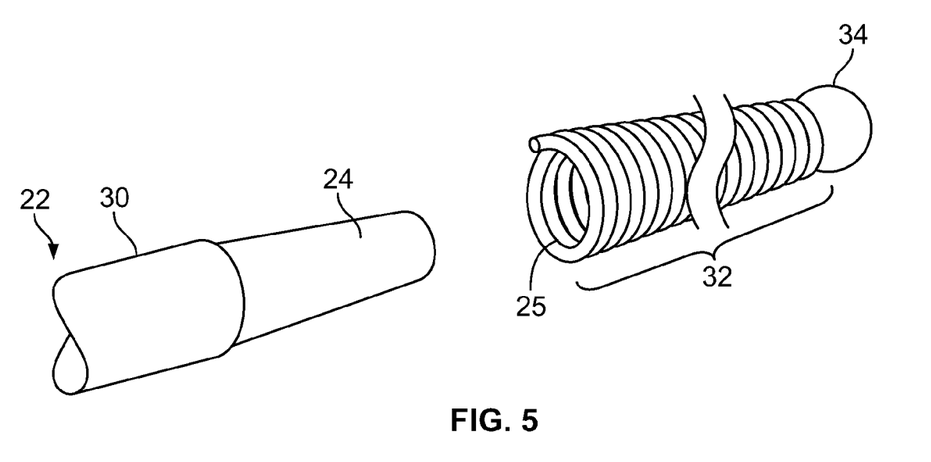
FIG. 5 is a perspective view to an enlarged scale of the distal end of the shock wave guide wire illustrating further aspects of the invention.
Figure 6:
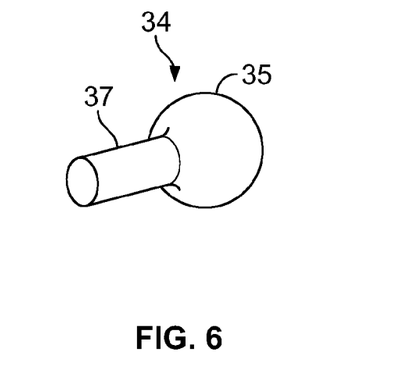
FIG. 6 is a perspective view, to an exploded scale, illustrating particular aspects of the distal tip electrode of the shock wave guide wire of FIG. 4.

FIG. 4 is a perspective view of the guide wire of the shock wave guide wire system of FIG. 1 illustrating further aspects of the invention. FIG. 5 is a perspective view to an enlarged scale of the distal end of the shock wave guide wire illustrating further aspects of the invention and FIG. 6 is a perspective view, to an exploded scale, illustrating particular aspects of the distal tip electrode of the shock wave guide wire of FIG. 4. As may be seen in FIG. 4, the guide wire includes the Tuehy-Borst connector 81 to anchor the insulator 30 and the elongated conductor 24. The electrode portion 32 of the guide wire 22 that does not include insulation may be milled to a finer diameter and then configured in a coiled configuration 33. This lends flexibility to the distal end 28 of the guide wire 22. The coiled configuration 33 is then terminated with the generally spherical electrode tip 34.

FIG. 5 shows an alternative manner of forming the coiled configuration in the electrode portion 32 of the guide wire 22. Here it may be seen that the elongated conductor 24 is tapered at its end and receives a separate coil 25 that is force fitted onto the taper of the conductor 24. The coil may include a thin layer of insulation, such Teflon. The electrode tip 34 may then be force fitted onto the distal end of the coil 25.

FIG. 6 shows structural details which the electrode tip may include. The electrode tip 34 may include a generally spherical portion 35 having an extension 37. The extension may be received within the coil 25. The conductor 24, the coil 25, and the electrode tip 34 may all be formed of stainless steel. Alternatively, the coil 25 may be formed of Teflon coated platinum and the electrode tip 34 may be formed of tungsten or other similar material. The elongated conductor may have a diameter of about 0.013 inch and the insulation may be formed of Teflon, for example and have a thickness of about 0.0005 inch. The guide wire may thus have an overall diameter of about 0.014 inch which is one common size for a guide wire. Also, the electrode tip may have a diameter of 0.008 to 0.014 inch. Still further, the electrode tip 34, instead of being ball shaped, may be formed of a single coil loop.

While heating of the blood and adjacent tissue may be controlled by adjusting the energy delivery of the high voltage pulses as described subsequently, active cooling of the therapy site is also an option. As shown in FIG. 3, saline may be introduced in the angioplasty balloon 80 to inflate it. That fluid could also be utilized for cooling purposes. Also, contrast could be added to the saline to provide visualization of the procedure. A 50/50 mix of saline and contrast would serve well. The cooling may be injected down the guide wire lumen and withdrawn as well and replenished in a cooling cycle using Luer connection 78. Advancing and withdrawing a saline solution has the added advantage of debris removal. Loose debris from the chronic total occlusion can be withdrawn with the fluid. Also, metal particles resulting from the arc therapy may be removed as well.

Figure 7:
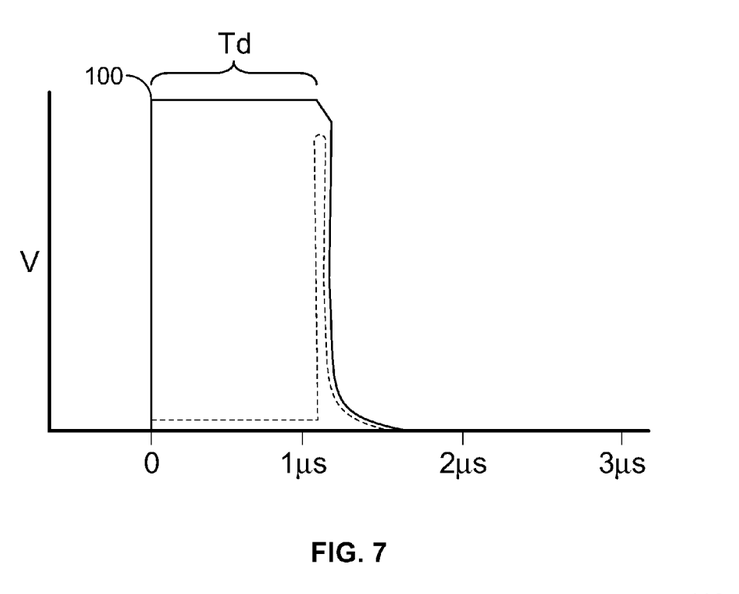
FIG. 7 is a graph illustrating a manner in which a shock wave guide wire system embodying the invention may be operated according to an embodiment of the invention.

FIG. 7 is a graph illustrating a manner in which a shock wave guide wire system embodying the invention may be operated according to an embodiment of the invention. As fully described in co-pending application Publ. No. 2014/0074113 filed on Sep. 13, 2012 for BALLOON SHOCK-WAVE CATHETER SYSTEM WITH ENERGY CONTROL, which application is owned by the assignee of the present invention and incorporated herein by reference in its entirety, it has been found that effective shock wave intensity may be accomplished without holding the high voltage pulses on during the entire extent of their corresponding steam bubbles. Moreover, terminating the application of the high voltage before steam bubble collapse can serve to preserve electrode material, permitting an electrode to last for an increased number of applied high voltage pulses. Also, early termination of the high voltage can also be used to advantage in controlling the temperature within the balloon fluid.

FIG. 7 is a graph illustrating a high voltage pulse applied to an electrical arc shock wave producing electrode and the resulting current flow through the electrode and it ground return in accordance with an embodiment of the invention. When the high voltage is first turned on, the voltage quickly rises to a level 100. During this time, as shown by dashed lines 102, the current is relatively low. After a dwell time (Td), the arc occurs at the electrode. At this time the steam bubble begins to form and a high current begins to flow. In accordance with embodiments of the invention, responsive to the current flow, the application of the high voltage is terminated. This conserves energy applied to the electrode, causing the electrode to remain useful for a greater number of pulses than otherwise would be the case if the high voltage were applied longer or sustained throughout the bubble existence. The temperature of the blood and adjacent tissue is also held to a lower than expected level because of the short duration of the applied energy. The advantages of controlling the applied energy in this manner are obtained without adversely affecting the intensity of the leading edge shock waves produced.

Figure 8:
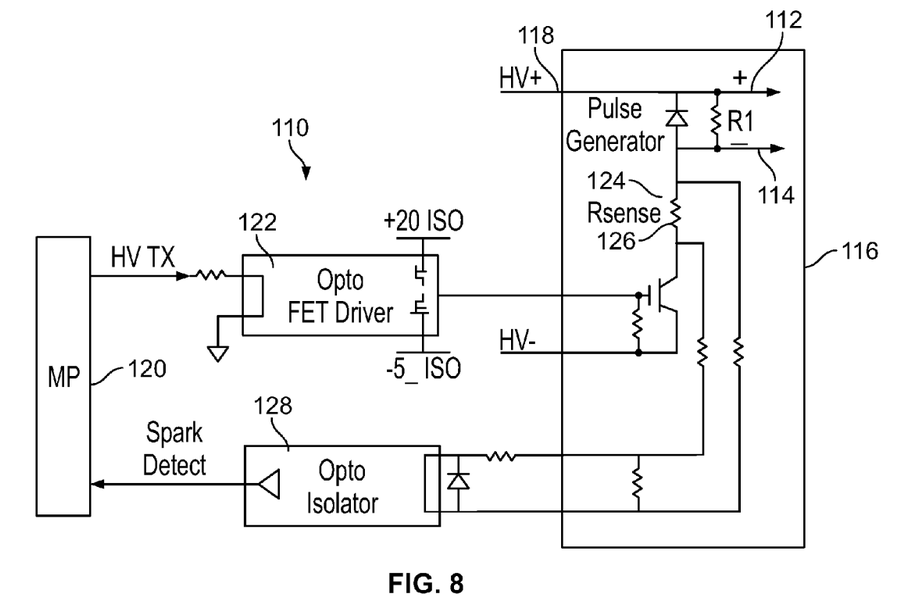
FIG. 8 is a schematic diagram of a power source for use in a shock wave guide wire system according to an embodiment of the invention.

FIG. 8 is a schematic diagram of a power source for use in a shock wave guide wire system according to an embodiment of the invention and which provides the operation shown in FIG. 7. The power source 110 has an output terminal 112 that may be coupled to the elongated conductor 24 of FIG. 1 and an output terminal 114 that may be coupled to the patch electrode 46 of FIG. 1. A switch circuit 116 selectively applies a high voltage on line 118 to the elongated conductor 24. A microprocessor 120, or other similar control circuitry, such as a gate array, controls the overall operation of the source 110. A Field Programmable Gate Array (FPGA) may also be substituted for the microprocessor in a manner known in the art. The microprocessor 120 is coupled to the switch 116 by an optical driver 122. The switch includes a current sensor 124 that includes a current sensing resistor 126 that generates a signal that is applied to an optical isolator 128 when the current flow reaches a predetermined limit, such as, for example, fifty (50) amperes.

In operation, the microprocessor 120 through the optical driver 122, causes the switch 116 to apply the high voltage to the elongated conductor 24, and thus the electrode tip 34 (FIG. 1). The current sensed through resister 126 is monitored by the microprocessor 120 through the optical isolator 128. When the current flow reaches a predetermined limit, as for example 50 amperes, the microprocessor 120 causes the application of the high voltage to be terminated. The forgoing occurs for each high voltage pulse applied to the elongated conductor 24 and thus the electrode tip 34. Each pulse creates a shock wave of consistent and useful intensity. Further, because the application of the high voltage is terminated early, the electrode material is preserved to lengthen the useful life of the electrodes and the heat generated is maintained at a low level.

Figure 9:
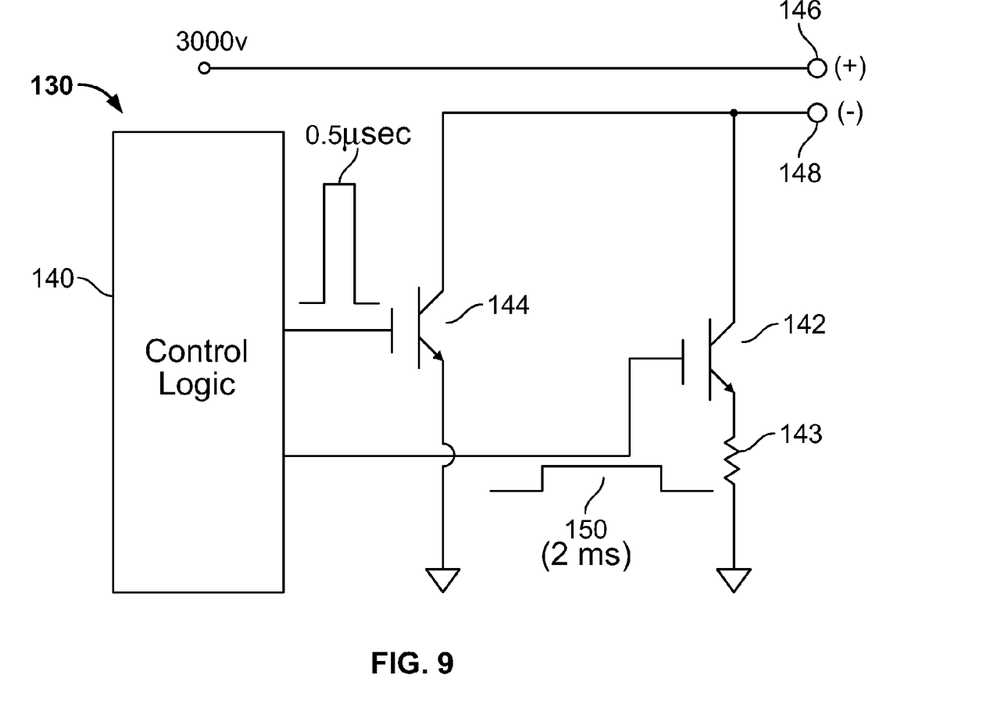
FIG. 9 is a schematic diagram of a power source for use in an a shock wave guide wire system according to another embodiment of the invention.

FIG. 9 is a schematic diagram of another power source 130 for use in an a shock wave guide wire system according to another embodiment of the invention. As will be seen, the power source 130 delivers a first low voltage across the elongated conductor 24 and the patch electrode 46 (FIG. 1) to pre-grow the bubble at the electrode tip 34 and thereafter delivers a second higher voltage to rapidly expand the pre-grown bubble to cause the arc and the shock wave in a time controlled manner.

The source 130 includes control logic 140, a first transistor 142, a second transistor 144, and output terminals 146 and 148. Output terminal 146 is arranged to coupled the elongated conductor 24 (FIG. 1) and output 148 is arranged to be coupled to the patch electrode 46. The output terminal 146 is connected to a 3,000 volt source.

Initially, the control logic 140 delivers a two millisecond (2 ms) control pulse 150 to the gate of transistor 142. This causes a low (for example, 25 ma) current through the elongated conductor 24 and the patch electrode 46 and a resistor 143. The low current applied for 2 ms forms a bubble on electrode tip 34 of a predictable size. After the 2 ms, the control logic 140 turns transistor 144 on hard for 500 nanoseconds (500 ns). This applies the full 3,000 volts to the elongated conductor. The control logic 140 may turn transistor 144 on hard immediately after the 2 ms period or a short time thereafter, as for example, 10 microseconds after the 2 ms period. An arc and shock wave will occur essentially immediately. Since the high voltage is applied for only a short time, here 500 ns, a reduced amount of energy is delivered. As a result, much less heat is generated.

Figure 10:
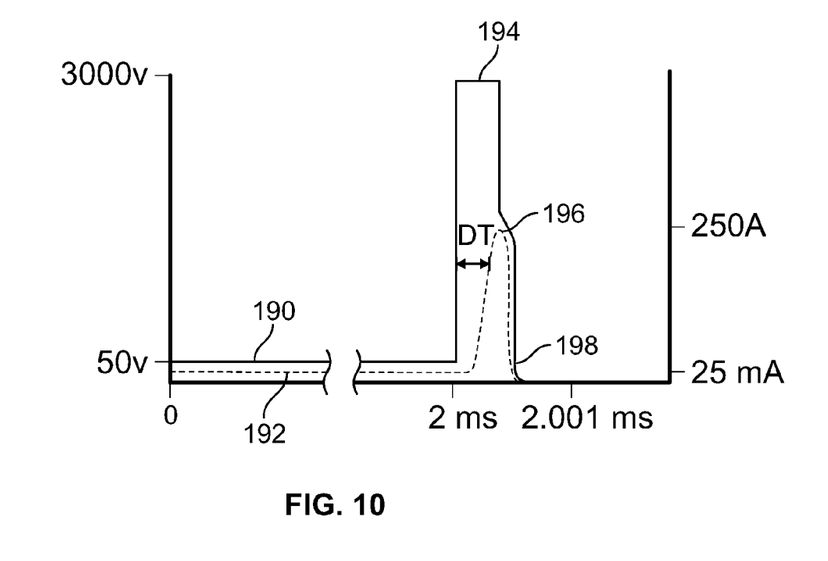
FIG. 10 is a graph illustrating another manner in which a shock wave guide wire system embodying the invention may be operated according to an embodiment of the invention with the power circuit of FIG. 9.

FIG. 10 is a graph illustrating another manner in which a shock wave guide wire system embodying the invention may be operated according to an embodiment of the invention with the power circuit of FIG. 9. First, a low voltage 190 is applied across the elongated conductor 24 and the patch electrode 46 when transistor 142 is turned on for 2 ms. The low voltage assures that an arc will not occur. However, the low voltage does produce a low current 192 (25 ma) to flow. During this 2 ms period, a bubble of predictable size is grown on electrode tip 34. The bubble size may be controlled by the amount of current and the length of time the low current is applied. After the 2 ms period, the transistor 144 is turned on hard to apply a narrow pulse (500 ns) of the full 3,000 volt high voltage 194. During this short time, a current of 250 amperes may flow. The high voltage and current rapidly expands the pre-grown bubble and within a short delay time DT causes the arc and shock wave to be produced at 196. The arc and shock wave are produced quickly because the bubble had already been pre-grown by the low voltage 90. The voltage and current fall quickly to zero at 198. For a more detailed discussion regarding the foregoing, reference may be had to co-pending application Publ. No. 2014/0052145 filed on Feb. 26, 2013 for SHOCK WAVE CATHETER SYSTEM WITH ARC PRECONDITIONING, which application is owned by the assignee of the present invention and incorporated herein by reference in its entirety.

As may be seen from the foregoing, the high voltage pulse is applied for a much shorter period of time to produce the arc and shock wave because the bubble had already been pre-grown by the preceding low voltage and current. The overall arc energy is lower and the steam bubble will be smaller. This results in less energy being applied and therefore less heat being generated.

While particular embodiments of the present invention have been shown and described, modifications may be made, and it is therefore intended to cover in the appended claims all such changes and modifications which fall within the true spirit and scope of the invention.

What is claimed:

1. A method for use in guiding an elongated catheter through an artery or vein of a mammalian body having a stenosis and/or an occlusion therein, the method comprising:
   providing an elongated guide wire having a longitudinal dimension, a proximal end and a distal end and an insulator overlying the elongated guide wire, the insulator configured to expose the distal end of the elongated guide wire to form a monopolar electrode;
   inserting the elongated catheter into an artery or vein to a point adjacent the stenosis and/or the occlusion;
   passing the guide wire through the catheter so that the distal end of the guide wire passes out through the distal end of the catheter directly into the vessel and adjacent the stenosis and/or the occlusion; and
   applying at least one high voltage pulse to the elongated guide wire, said voltage pulse being between about 300 and 3000 volts and between 0.1 to 2.0 microseconds in duration to cause at least one electrical arc at the electrode that in turn forms at least one steam bubble and a shock wave to break the stenosis and/or open the occlusion.

2. The method of claim 1, wherein the step of applying the at least one high voltage pulse to the elongated guide wire includes providing the elongated guide wire with a high electrical voltage at a comparatively low initial current through the elongated guide wire and terminating the high electrical voltage in response to a comparatively high current through the elongated guide wire.

3. The method of claim 1, wherein the step of applying the at least one high voltage pulse to the elongated guide wire includes delivering a first electrical voltage to the electrode that begins to grow the at least one steam bubble at the electrode and then thereafter delivering a second electrical voltage higher than the first voltage to the electrode to create the arc at the electrode and to rapidly expand the at least one steam bubble to form the shock wave.

4. A method for opening a vascular occlusion comprising:
   advancing a shock wave guide wire within the vasculature to contact the vascular occlusion, wherein the shock wave guide wire comprises an elongated conductor with a conductive distal tip defining a monopolar electrode and an insulator overlying the elongate conductor without covering the conductive distal tip;
   advancing an angioplasty balloon catheter over the shock wave guide wire to the vascular occlusion;
   applying at least one high voltage pulse to the guide wire, said voltage pulse being between about 300 and 3000 volts and between 0.1 to 2.0 microseconds in duration to cause at least one electrical arc at the electrode that in turn forms at least one steam bubble and a shock wave to create one or more openings in the occlusion; and
   advancing the angioplasty balloon catheter into the one or more openings to perform an angioplasty procedure.

5. The method of claim 4, further comprising visualizing the vascular occlusion.

6. The method of claim 5, wherein visualizing the vascular occlusion comprises injecting a dye from the angioplasty balloon catheter.

7. The method of claim 6, further comprising confirming the location of the shock wave guide wire and/or the angioplasty balloon catheter prior to generating one or more shock waves.

8. The method of claim 4, further comprising centering the distal tip of the shock wave guide wire within the vascular lumen prior to applying the high voltage pulse.

9. The method of claim 8, wherein centering the distal tip of the shock wave guide wire comprises expanding the angioplasty balloon of the angioplasty balloon catheter.

10. The method of claim 4, wherein advancing the angioplasty balloon catheter into the one or more openings to perform an angioplasty procedure comprises inflating the balloon to further open the occlusion.

11. The method of claim 4, wherein the angioplasty balloon catheter comprises one or more shock wave electrodes within the balloon and wherein advancing the angioplasty balloon catheter into the one or more openings to perform an angioplasty procedure comprises generating one or more shock waves within the angioplasty balloon to further open the occlusion.

12. A method for opening a vascular occlusion comprising:
   advancing a shock wave guide wire within the vasculature to contact the vascular occlusion, wherein the shock wave guide wire comprises an elongated conductor with a conductive distal tip defining a monopolar electrode and an insulator overlying the elongate conductor without covering the conductive distal tip; and
   generating one or more shock waves using the guide wire to create one or more openings in the occlusion wherein each shock wave is generated by applying a high voltage pulse to the guide wire, said voltage pulse being between about 300 and 3000 volts and between 0.1 to 2.0 microseconds in duration to create an electrical arc at the electrode that in turn forms at least one steam bubble and a shock wave.

13. The method of claim 12, further comprising visualizing the vascular occlusion prior to generating one or more shock waves.

14. The method of claim 12, further comprising advancing an angioplasty balloon catheter over the shock wave guide wire to the one or more openings in the vascular occlusion to perform an angioplasty procedure.

15. The method of claim 14, wherein the angioplasty balloon catheter comprises one or more shock wave electrodes within the balloon and wherein advancing the angioplasty balloon catheter into the one or more openings to perform an angioplasty procedure comprises generating one or more shock waves within the angioplasty balloon to further open the occlusion.

16. The method of claim 12, further comprising centering the distal tip of the shock wave guide wire within the vascular lumen prior to generating one or more shock waves.

17. The method of claim 16, wherein centering the distal tip of the shock wave guide wire comprises expanding the angioplasty balloon of the angioplasty balloon catheter.

* * * * *